(12) United States Patent
Dion

(10) Patent No.: US 7,472,613 B2
(45) Date of Patent: Jan. 6, 2009

(54) DEVICE AND METHOD FOR MEASURING METAL INCLUSIONS

(75) Inventor: Serge Dion, St-fereole-les-neiges (CA)

(73) Assignee: Alcan International Limited, Montreal, Quebec (CA)

( * ) Notice: Subject to any disclaimer, the term of this patent is extended or adjusted under 35 U.S.C. 154(b) by 352 days.

(21) Appl. No.: 10/555,505

(22) PCT Filed: Apr. 22, 2004

(86) PCT No.: PCT/CA2004/000601

§ 371 (c)(1),
(2), (4) Date: Jun. 1, 2006

(87) PCT Pub. No.: WO2004/099769

PCT Pub. Date: Nov. 18, 2004

(65) Prior Publication Data

US 2006/0236790 A1 Oct. 26, 2006

(51) Int. Cl.
*G01N 1/12* (2006.01)
(52) U.S. Cl. .................................. 73/864.54; 73/864.58
(58) Field of Classification Search .............. 73/864.54, 73/864.58
See application file for complete search history.

(56) References Cited

U.S. PATENT DOCUMENTS

| | | | | |
|---|---|---|---|---|
| 3,255,634 A | * | 6/1966 | Cavalier | ................... 73/864.54 |
| 3,309,928 A | * | 3/1967 | Cavalier | ................... 73/864.54 |
| 4,624,929 A | * | 11/1986 | Ullman | ................. 73/864.54 X |
| 5,139,238 A | | 8/1992 | Buhr | |
| 5,827,982 A | | 10/1998 | Doutre et al. | |
| 5,894,085 A | | 4/1999 | Roberge et al. | |

FOREIGN PATENT DOCUMENTS

| | | |
|---|---|---|
| GB | 2 306 896 A | 5/1997 |
| GB | 2 307 049 A | 5/1997 |
| JP | 59-202063 | 11/1984 |

OTHER PUBLICATIONS

Patent Abstract of Japan; vol. 2000, No. 16, May 8, 2001 & JP 2001 026828 A (Nippon Light Metal Co. Ltd), Jan. 30, 2001 abstract and clipped image only.

* cited by examiner

*Primary Examiner*—Thomas P Noland
(74) *Attorney, Agent, or Firm*—RatnerPrestia

(57) ABSTRACT

A device is provided for measuring metal inclusions comprising a receptacle for holding a sample of molten metal, with this receptacle having insulated side walls and a bottom wall provided with an exit opening. A ceramic filter element for collecting inclusions from the molten metal is positioned within the exit opening and is bonded to the top face of a solid refractory or metal annular support ring with a portion of the support ring top face extending laterally beyond the filter element and engaging the bottom face of the bottom wall of the receptacle around the opening. The filter element and support ring assembly is held in place by a detachable retaining means which is adapted to securely hold the support ring in leak-tight engagement against the receptacle bottom wall with the filter element positioned in the exit opening.

17 Claims, 2 Drawing Sheets

DEVICE AND METHOD FOR MEASURING METAL INCLUSIONS

TECHNICAL FIELD

This invention relates to a particle measuring device for allowing capture and measure of solid particles in samples of molten metal, in particular in molten aluminum in cast houses and foundries.

BACKGROUND ART

It is known in the art of cast houses and foundries that production and refining of metals and remelting of metals inevitably results in what, for convenience in nomenclature, are referred to as "inclusions" or "solid particles", such as precipitated secondary phase particles, drops of slag, oxides and the like which have a more or less deleterious effect upon the technical properties of the metals. The presence of such inclusions within the resultant rolled or cast products is generally undesirable from the point of view of properties such as fatigue life, toughness, corrosion, tearing, splitting, surface quality, pinholes, etc., particularly when larger inclusions (e.g., dimensions >20 microns) are present. It has therefore become more and more essential to know whether or not the metal is sufficiently "clean" for its intended purpose, and also identify the nature, and hence source of such inclusions.

U.S. Pat. No. 5,827,982 (Doutre et al.) discloses a device for measuring metal purity, comprising a receptacle to which is internally secured a filter element through which passes the molten metal drawn by vacuum to provide samples to be analyzed for inclusion.

GB 2307049 (Enright) discloses a device for measuring metal purity, comprising a receptacle into which is secured a filter element inside the receptacle at the outlet through which passes molten metal forced by an applied pressure.

GB 2306896 (Enright) discloses an insulated crucible with a filter element mounted at the outlet end but inside the vessel for use in measuring metal purity.

JP 59-202063 (Koichiro et al.) discloses an apparatus for measuring metal purity, comprising a heated crucible with an internally mounted filter element at the outlet which is filled with metal and pressurized to cause metal to flow through the filter for analysis.

The above methods of metal analysis all use filter elements mounted internally in the receptacle and which either cannot be readily separated from the crucible when the solidified metal is removed or take time and effort to replace.

It is therefore an objective of the present invention to provide a reusable crucible with an inexpensive and simple means for mounting a filter therein to permit the measurement of metal purity and identify the specific inclusions.

DISCLOSURE OF THE INVENTION

In one aspect the present invention relates to a device for measuring metal inclusions comprising a receptacle for holding a sample of molten metal, with this receptacle having insulated side walls and a bottom wall provided with an exit opening. A ceramic filter element for collecting inclusions from the molten metal is positioned within the exit opening and is bonded to the top face of a solid refractory or metal annular support ring with a portion of the support ring top face extending laterally beyond the filter element and engaging the bottom face of the bottom wall of the receptacle around the opening. The filter element and support ring assembly is held in place by a detachable retaining means which is adapted to securely hold the support ring in leak-tight engagement against the receptacle bottom wall with the filter element positioned in the exit opening.

In another aspect, the present invention relates to a method for measuring metal inclusions using the above described device. According to the method, the receptacle is filled with molten metal to a predetermined level. Then, either pressure is applied to the top of the receptacle or vacuum is applied to the bottom of the receptacle to force the molten metal to pass through the filter element. When the receptacle has been emptied, any residual molten metal in the bottom of the receptacle, including molten metal in and around the filter element, is allowed to solidify. The detachable retaining means is then removed and a lateral force is applied to the support ring thereby shearing the bond with the filter. Thereafter, the filter element and residual metal are removed, with the filter providing an optimum sample for subsequent metallographic analysis.

In a still further aspect, the invention relates to a filter assembly for use in measuring metal inclusions in molten metal passed through the filter. This assembly includes a ceramic filter element for collecting inclusions from the molten metal and a solid refractory or metal annular support ring for supporting the filter. The support ring has a central opening with a diameter less than that of the filter element and an outer diameter greater than that of the filter element. A bonding agent between the filter element and the support ring serves to bond the filter and support together. This assembly can be manufactured as a unit and is used for inserting a fresh filter element into the bottom exit opening of the molten metal receptacle at the start of a test.

It has been found to be advantageous to make the diameter of the filter element slightly less than the diameter of the exit opening so as to provide a peripheral gap between the edge of the filter element and the edge of the opening. When the receptacle has been emptied of molten metal, some residual metal remains in the peripheral gap and solidifies. This securely holds the filter within the opening so that when the shearing force is applied to the support ring a clean fracture occurs along the bond line. Thereafter the filter element and residual solidified metal are easily removed from the exit opening.

According to a preferred feature of the invention, an impermeable coating is applied to part of the top surface of the filter element and on the sides of the filter element where it is desired that molten metal not flow. An uncoated central portion of the filter is left for the molten metal flow. The coating used is preferably a metal resistant refractory material.

According to a further preferred feature, the receptacle is of a double wall design having an inner wall that tapers inwardly toward the bottom exit opening, with the space between the inner and outer walls being filled with insulating material. By shaping the inner wall in this manner, at the end of a test when the receptacle is emptied of molten metal, the only residual solidified metal not contained within the filter itself is to be found in the peripheral gap between the edge of the filter element and the edge of the opening.

The support ring is preferably an annular steel ring with a central opening through which the molten metal passes after passing through the filter. To assure a leak-tight seal between the support ring and the bottom of the receptacle, a gasket made of refractory fiber may be used between the support ring top face and the receptacle bottom.

For firmly holding the support ring in place, it is preferable to provide within the bottom wall of the receptacle an axially positioned cylindrical recess or socket extending upwardly into the bottom wall. The top end of this bottom socket then becomes the bottom wall portion of the receptacle containing the exit opening and also connecting to the bottom end of the inwardly tapered inner wall of the receptacle. The detachable retaining means can then be in the form of a threaded ring mating with threads in the walls of the socket or it can be in the form of a bayonet connector mating with tabs projecting from the socket wall. The bayonet type connection has the advantage that it is not affected by distortion or mismatch which may occur under repeated high temperature use. At the same time, the bayonet type connection serves to firmly hold the filter support ring in place and prevent leakage of molten metal around the filter under the applied pressure or vacuum.

A variety of known ceramic materials may be used for the filter element itself. However, for quantitative analysis it is important that a single type of ceramic material be chosen since the quantity and nature of inclusion trapped by a particular filter type will vary and each filter type must therefore be recalibrated. For the purposes of this invention the filter element has average pore sizes in the range of about 100 to 140 microns.

The measuring device of this invention is particularly useful for the testing of aluminum samples. Thus, the coatings, bonding agents, etc. that are used should be resistant to molten metal and its alloys at temperatures up to about 800° C.

BRIEF DESCRIPTION OF THE DRAWINGS

In the drawings which show preferred embodiments of the present invention.

BEST MODES FOR CARRYING OUT THE INVENTION

Figure 1:
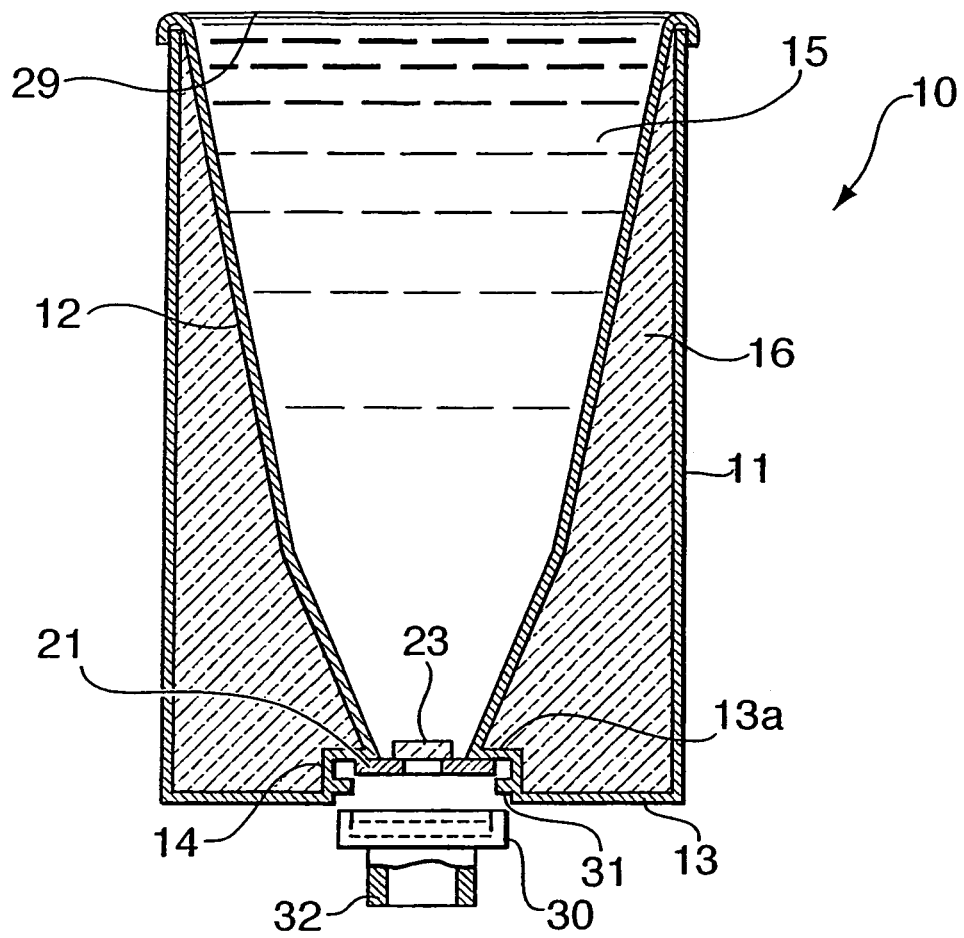
FIG. 1 is a vertical cross-section showing generally the device of the invention.

As can be seen generally in FIG. 1, a testing device 10 is formed having a cylindrical external steel wall 11, a bottom steel wall 13 and a generally conically shaped interior stainless steel wall 12 ending in a bottom exit opening 27. The space between the inner and outer walls is filled with insulating material 16. A coating such as a layer of boron nitride may be applied to the inner surface of the wall 12 to prevent molten metal sticking.

A cylindrical recess or socket 14 is formed into bottom wall 13 providing an inner bottom wall portion 13*a* which joins the bottom end of inner wall 12 and within which is formed the bottom exit opening 27.

Figure 2:
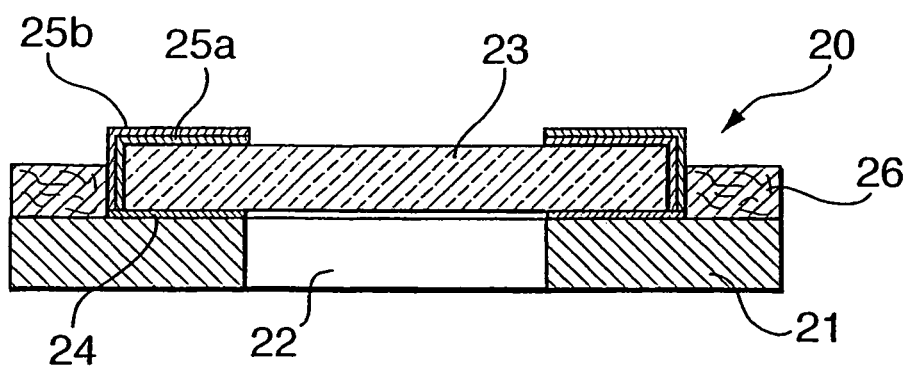
FIG. 2 is a vertical section of a filter element and support ring assembly according to the invention.
Figure 3:
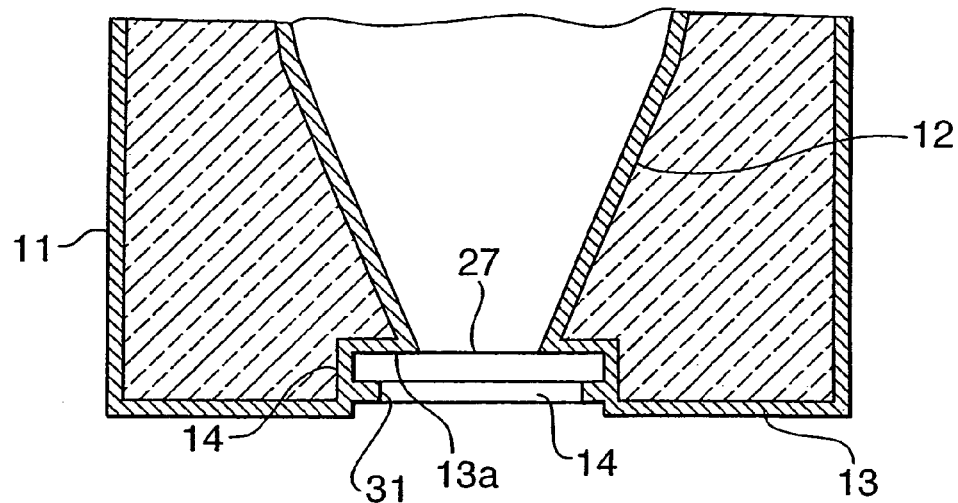
FIG. 3 is a vertical section showing the bottom socket portion of the device.

Details of the filter assembly can be seen in FIG. 2. It includes a filter element 23 of known type as described above. It preferably has an average pore diameter size of about 120 microns. The filter element has a diameter slightly less than the diameter of the exit opening 27 and is mounted on an annular steel ring 21 having a central opening 22 and an outer diameter greater than the diameter of the exit opening 27. The filter element 23 is fixed to the top face of the ring 21 by a bonding agent or glue 24 that is resistant to molten aluminum at temperatures up to about 800° C., with a good high temperature strength and a thermal conductivity similar to that of steel. It should, however, be susceptible to shearing under force. A typical glue for this purpose is Resbond® 918 manufactured by Cotronics.

Before bonding the filter element 23 to the ring 21 by the bonding agent or glue 24, a portion of the filter element 23 is covered by an impermeable coating 25. This coating covers part of the top surface of the filter element as well as the side surfaces of the element where molten metal is not desired to flow. This leaves a central portion of the filter element 23 in alignment with the central opening of the ring 22 through which the molten metal is permitted to flow. The coating 25 is preferably a metal resistant refractory coating such as a two layer coating as shown in FIG. 2 in which a first layer 25*a* provides an impermeable seal to the material and a second layer 25*b* protects the first layer 25*a* from molten metal attack. An example of such a combination is Holocote® 555 manufactured by Foseco overlaying a cement such as an alumino-silicate cement, e.g. QF-150 supplied by Unifrax Corporation. The underlying QF-150 layer 25*a* renders the material impermeable, and the Holcote-555 overlayer 25*b* protects the QF-150 layer from molten metal attack.

Figure 4:
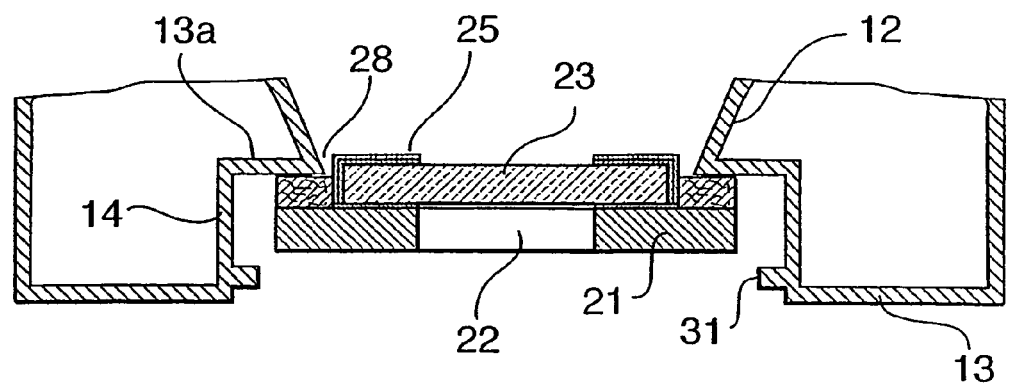
FIG. 4 is an enlarged vertical sectional view showing a filter element assembly mounted in the bottom socket.

The filter assembly is placed within the socket 14 and exit opening 27 as seen in FIGS. 1 and 4. In order to assure a leak-tight mounting, a refractory fiber annular gasket 26 is mounted between the top face of the steel ring 21 and the bottom wall 13*a*. For convenience, this gasket 26 may be fixed to the annular steel ring using a cement such as QF-150.

A mounting ring is used to hold the filter assembly in place, this mounting ring being adapted to press upwardly against the bottom face of the support ring 21 and thereby compress the gasket 26 against the bottom wall portion 13*a* to assure a leak-tight connection. The mounting ring 30 is preferably in the form of a bayonet connector mating with projecting tabs 31 within the socket 14. This provides for easy installation and/or removal of the filter assembly. A flow connector portion 32 connects to the mounting ring 30 and serves to connect testing device 10 to a receiving vessel.

In use, the receptacle is filled to the filling mark 29 with molten aluminum or aluminum alloy to be tested. Then, in known manner either pressure is applied to the top face of the aluminum in the receptacle or a vacuum is applied to a receiving vessel beneath the receptacle to thereby force the aluminum 15 through the filter element 23. Examples of arrangements for applying vacuum or pressure can be found in U.S. Pat. No. 5,827,982 and British Patent 2,307,049, respectively. When all of the molten aluminum 15 has passed through the filter element, the remaining molten aluminum within the filter element and within the annular gap 28 surrounding the filter element 23 is allowed to solidify.

At this point the mounting ring 30 is removed and a small lateral force is applied to the steel ring 21 causing a fracture to occur along the glue line 24. A clean fracture between the steel ring 21 and the filter element 23 is aided by the ring of solidified aluminum in the gap 28 which prevents any lateral movement of the filter element 23 while the lateral force is being applied to the ring 21.

The filter and residual solidified aluminum are then removed downwardly from the bottom, with the filter providing an optimum sample for subsequent metallographic analysis. A fresh filter and support ring assembly can then be inserted into the bottom socket and exit opening and a further test can be conducted.

The invention claimed is:

1. A device for measuring metal inclusions, comprising:
   a receptacle for holding a sample of molten metal, said receptacle having insultated side walls and a bottom wall provided with an exit opening,
   a ceramic filter element for collecting inclusions from said molten metal, said filter element being positioned in said exit opening, and said filter element being bonded to the top face of a solid refractory or metal annular support ring with a portion of said support ring top face extending laterally beyond the filter element and engaging the bottom face of the bottom wall of the receptacle around said opening, and detachable retaining means for securely holding the support ring in leak-tight engagement against the receptacle bottom wall with the filter element positioned in the bottom exit opening.

2. The device of claim 1, wherein a peripheral gap is provided between the edge of the filter element and the edge of the opening.

3. The device of claim 1, wherein the support ring is an annular steel ring.

4. The device of claim 1, wherein the receptacle has inner walls that taper inwardly toward the bottom exit opening.

5. The device of claim 1, wherein portions of the filter element are coated with an impermeable layer resistant to molten metal, leaving a central portion uncoated for passage of the molten metal.

6. The device of claim 5, wherein a refractory fibre gasket is provided between the support ring top face and the receptacle bottom.

7. The device of claim 1, wherein the filter element is bonded to the support ring and is adapted for separation by a shearing action.

8. The device of claim 1, wherein the receptacle comprises a cylindrical outer wall, a generally conical inner wall and insulation between said inner and outer walls.

9. The device of claim 1, wherein the bottom wall includes an axial cylindrical recess with the bottom exit opening located within the recess.

10. The device of claim 9, wherein the detachable retaining means is a bayonet mounting ring which engages the bottom of the support ring within the bottom recess.

11. The device of claim 1, wherein the receptacle has an open top and the exit opening connects to a receiving vessel adapted to have vacuum applied thereto.

12. The device of claim 1, wherein the receptacle has a closed top and includes means for applying pressure thereto.

13. The device of claim 1, wherein the ceramic filter element has average pore sizes in the range of about 100 to 140 microns.

14. A method of measuring metal inclusions, comprising:

providing a device having a receptacle with insulated side walls and a bottom wall provided with an exit opening, a ceramic filter element for collecting inclusions positioned in said exit opening, said filter element being bonded to the top face of a solid refractory or metal annular support ring with a portion of said support ring top face extending laterally beyond the filter element and engaging the bottom face of the bottom wall of the receptacle and detachable retaining means for securely holding the support ring in leak-tight engagement against the receptacle bottom wall with the filter element positioned in the bottom exit opening, said method comprising the steps of filling the receptacle with molten metal to be tested, applying pressure to the top of the receptacle or vacuum to the bottom of the receptacle to cause the molten metal to pass through the filter element, when the receptacle has been emptied allowing residual molten metal in the bottom of the receptacle, including molten metal in and around the filter element, to solidify, removing the detachable retaining means, applying a lateral force to the support ring thereby shearing the bond with the filter and thereafter removing the filter element and residual metal and separating the filter element for analysis.

15. The method of claim 14, wherein the molten metal is molten aluminum or alloys thereof.

16. The method of claim 14, wherein the molten metal is passed through a ceramic filter element having average pore sizes in the range of about 100 to 140 microns.

17. The method of claim 14, wherein the walls retaining the molten metal taper downwardly toward the bottom exit opening and a peripheral gap is provided between the edge of the filter element and the edge of the opening such that said residual solidified metal is present substantially only within the ceramic filter element anmd within the peripheral gap adjacent the filter element.

* * * * *

UNITED STATES PATENT AND TRADEMARK OFFICE
CERTIFICATE OF CORRECTION

PATENT NO. : 7,472,613 B2  
APPLICATION NO. : 10/555505  
DATED : January 6, 2009  
INVENTOR(S) : Serge Dion Page 1 of 1

It is certified that error appears in the above-identified patent and that said Letters Patent is hereby corrected as shown below:

Column 6, Line 39 "anmd" should read "and"

Signed and Sealed this

Twenty-fourth Day of March, 2009

JOHN DOLL  
*Acting Director of the United States Patent and Trademark Office*